United States Patent [19]
Aldous

[11] Patent Number: 5,543,136
[45] Date of Patent: Aug. 6, 1996

[54] SUNSCREEN EMULSIONS

[75] Inventor: Duane L. Aldous, Orem, Utah

[73] Assignee: NuSkin International, Inc., Provo, Utah

[21] Appl. No.: 260,568

[22] Filed: Jun. 16, 1994

[51] Int. Cl.$^6$ ............................................. A61K 7/42
[52] U.S. Cl. ............................................. 424/59
[58] Field of Search ............................................. 424/59

[56] References Cited

U.S. PATENT DOCUMENTS

| | | | |
|---|---|---|---|
| 4,036,951 | 7/1977 | Halpern et al. | 424/59 |
| 4,172,122 | 10/1979 | Kubik et al. | 424/59 |
| 4,184,978 | 1/1980 | France et al. | 424/59 |
| 4,250,315 | 2/1981 | Poncioni | 424/59 |
| 4,284,630 | 8/1981 | Yu et al. | 424/59 |
| 4,749,563 | 6/1988 | Georgalas | 424/59 |
| 4,781,914 | 11/1988 | Deckner | 424/59 |
| 4,793,990 | 12/1988 | Grollier et al. | 424/59 |
| 5,009,969 | 4/1991 | Miller | 424/59 |
| 5,015,469 | 5/1991 | Yoneyama et al. | 424/59 |
| 5,093,107 | 3/1992 | Matravers | 424/59 |
| 5,256,422 | 10/1993 | Albert et al. | 424/59 |

OTHER PUBLICATIONS

Mitchnick, Mark A., "Zinc Oxide, An Old Friend to the Rescue", Cosmetics & Toiletries., Mar. 3, 1993.
Product Description Sheet for UV–TITAN from Presperse Inc., no date.
"Proposed Rules", Federal Register, vol. 58, No. 90, p. 28231, May 12, 1993.
"Proposed Rules", Federal Register, vol. 58 No. 90, p. 28295, May 12, 1993.
"Proposed Rules", Federal Register, vol. 58, No. 90 p. 28296, May 12, 1993.
Sellers et al., "An Instrument for In–Vitro Determinations of SPF", Cosmetics & Toiletries, vol. 107, pp. 119–123, Oct. 1992.
"Topical Drugs", Remington's Pharmaceutical Sciences 16, Chapter 39, pp. 722–723, 732–733, 1980.
Trivent Chemical Company, Inc. "Trivent NP–13 SPF Booster", Technical Bulletin., Apr. 1992.
"Using the Encyclopedia of UV Absorbers for Sunscreen Products", Cosmetic & Toiletries, vol. 107, p. 48, Oct. 1992.
"sunSmart Formulation: 6530/1", SunSmart, Inc.

Primary Examiner—Shelley A. Dodson
Attorney, Agent, or Firm—Trask, Britt & Rossa

[57] ABSTRACT

Disclosed are sunscreen emulsions, especially water-in-oil emulsions, containing zinc oxide and titanium dioxide in the continuous and discontinuous phases of the emulsion, respectively. The emulsions contain an agent such as tridecyl neopentanoate and also contain agents in sufficient quantities to form an oil phase that will produce an emulsion having a smooth and continuous appearance. Methods of making and processes for use of the emulsions are also disclosed.

17 Claims, 1 Drawing Sheet

SUNSCREEN EMULSIONS

TECHNICAL FIELD

The invention relates generally to topical radiation screening and tanning preparations, and more specifically to sunscreen emulsions including zinc oxide in the emulsion's continuous phase, and titanium dioxide in the emulsion's discontinuous phase.

BACKGROUND ART

It is well known that light radiation having a wavelength of between 280 and 320 nm causes erythema and skin burns, the effects of which increase according to the length of exposure. A suitable protective agent should accordingly absorb light radiation in the zone from about 280 to 320 nm. "Emulsions," as used herein, is a system which includes a liquid (e.g. an oil) dispersed in an immersible liquid (e.g. water). As such, an emulsion has two phases, a continuous phase and a discontinuous phase. In the case of an oil-in-water emulsion, oil is the discontinuous phase, and water is the continuous phase. Hydrophobic constituents of the emulsion tend to concentrate in the oil phase, while hydrophilic constituents tend to concentrate in the water (or aqueous) phase. Water-in-oil emulsions have been described for use as vehicles for sunscreen agents. When water-in-oil emulsions are applied to the skin, the water-phase droplets are believed to be suspended in a film of oil. This film is believed to create a moisturizing and non-hygroscopic barrier, which does not take up water, thus deterring the emulsion from being washed off.

U.S. Pat. No. 4,284,630 to Yu et al. (Aug. 18, 1981) discloses stable water-in-oil emulsions useful as vehicles for cosmetics or for application of medicinal compositions. The emulsions use magnesium oxide or magnesium hydroxide as a stabilizing agent, which permit the incorporation of up to 70% water in the total composition without loss of shelf-life stability. The emulsions create a water non-washable dispersion medium, which possess substantiation and occlusion properties after application to the skin.

U.S. Pat. No. 4,781,914 to Deckner (Nov. 1, 1988) discloses a moisture-resistant skin treatment composition in the form of a sprayable oil-in-water emulsion that inverts to a water-in-oil emulsion upon being robbed onto the skin. The invention uses polyglyceril-8 oleate as an emulsifier to impart moisture resistance to the skin treatment composition.

U.S. Pat. No. 5,256,422 to Albert et al. (Oct. 26, 1993) discloses a water-in-oil emulsion having a discontinuous aqueous phase dispersed within a continuous oil phase. The aqueous droplets forming the discontinuous aqueous phase have intact liposomes dispersed therein, thus forming a type of oil-in-water-in-oil emulsion. The invention allows incorporation of aqueous soluble materials into either the aqueous phase external to the lipid vesicles or into the lipid vesicles themselves. Likewise, any oil soluble materials can be included into the emulsion via the continuous oil phase or the lipid vesicles.

Sunscreen preparations, which extend the time of exposure needed to produce a sunburn, are also commercially available. Such preparations contain ultraviolet absorbing chemicals such as the alkyl esters of aminosalicylic acid disclosed in U.S. Pat. No. 4,036,951 to Halpern et al. (Jul. 19, 1977), the benzoxazole derivatives in U.S. Pat. No. 4,250,315 to Poncioni (Feb. 10, 1981), and the coffee bean oil in U.S. Pat. No. 4,793,990 to Grollier et al. (Dec. 27, 1988).

Physical sunscreens generally include heavy creams or pastes containing such compounds as ZnO and $TiO_2$. Although physical sunscreens reflect and scatter radiation effectively, such sunscreens create an opaque film and thus lack cosmetic appeal.

The art is not believed to suggest that by carefully choosing various ingredients and incorporating them into specific phases of a selected emulsion that a synergistic combination would result.

DISCLOSURE OF THE INVENTION

Surprisingly, it has been found that by incorporating $TiO_2$ into the discontinuous phase of an emulsion, and ZnO in the continuous phase of the same emulsion, that a synergistic combination results.

Further, it has been found that a water-in-oil emulsion containing titanium dioxide in the water phase of the emulsion, zinc oxide in the oil phase of the emulsion, together with a compound such as tridecyl neopentanoate (e.g. $C_{12-5}$ alkyl benzoate or octyl neopentanoate), and sunblocking agents, results in an especially advantageous emulsion having an exceedingly high sun protection factor (SPF) value. In particular, the invention concerns the use of ZnO, $TiO_2$, and organic agents for the purpose of enhancing the SPF of a water-in-oil emulsion. The SPF value is the ultraviolet energy required to produce a minimal erythema dose ("MED") on protected skin, divided by the ultraviolet energy required to produce an MED on unprotected skin. An MED is the smallest dose of ultraviolet radiation that produces redness reaching the borders of the exposure site. The emulsion is primarily useful as a sun screening agent and moisturizer for application to the skin.

The emulsion typically contains ZnO and an agent such as tridecyl neopentanoate in the oil phase of the emulsion, $TiO_2$ in the water phase of the emulsion, and sunblocking agents as basic ingredients. Other ingredients which also may be included are thickeners, emulsifying agents, moisturizers, emollients, preservatives, coloring agents, fragrances, antioxidants and the like.

Surprisingly, the water-in-oil emulsion displays an improved "SPF" value, which is higher than the value seen in analogous emulsions having ZnO and $TiO_2$ in the opposite phases (i.e. ZnO in the water phase and $TiO_2$ in the oil phase) in a water-in-oil emulsion having $TiO_2$ and ZnO in the same phases or in an oil-in-water emulsion having similar ingredients. The emulsion filters light radiation from about 280 to about 320 nm. Additionally, the emulsion creates a transparent (i.e. non-whitening), moisture-resistant medium, which possesses occlusive and moisturizing properties after application to the skin.

The invention also includes processes of making and using such emulsions. The process may be used to manufacture an emulsion for the prevention of a sunburn. An inventive emulsion may be topically applied to a mammal, such as a human, before prolonged exposure to light radiation to prevent the erythema normally observed after such exposure.

BEST MODE OF THE INVENTION

Figure 1:
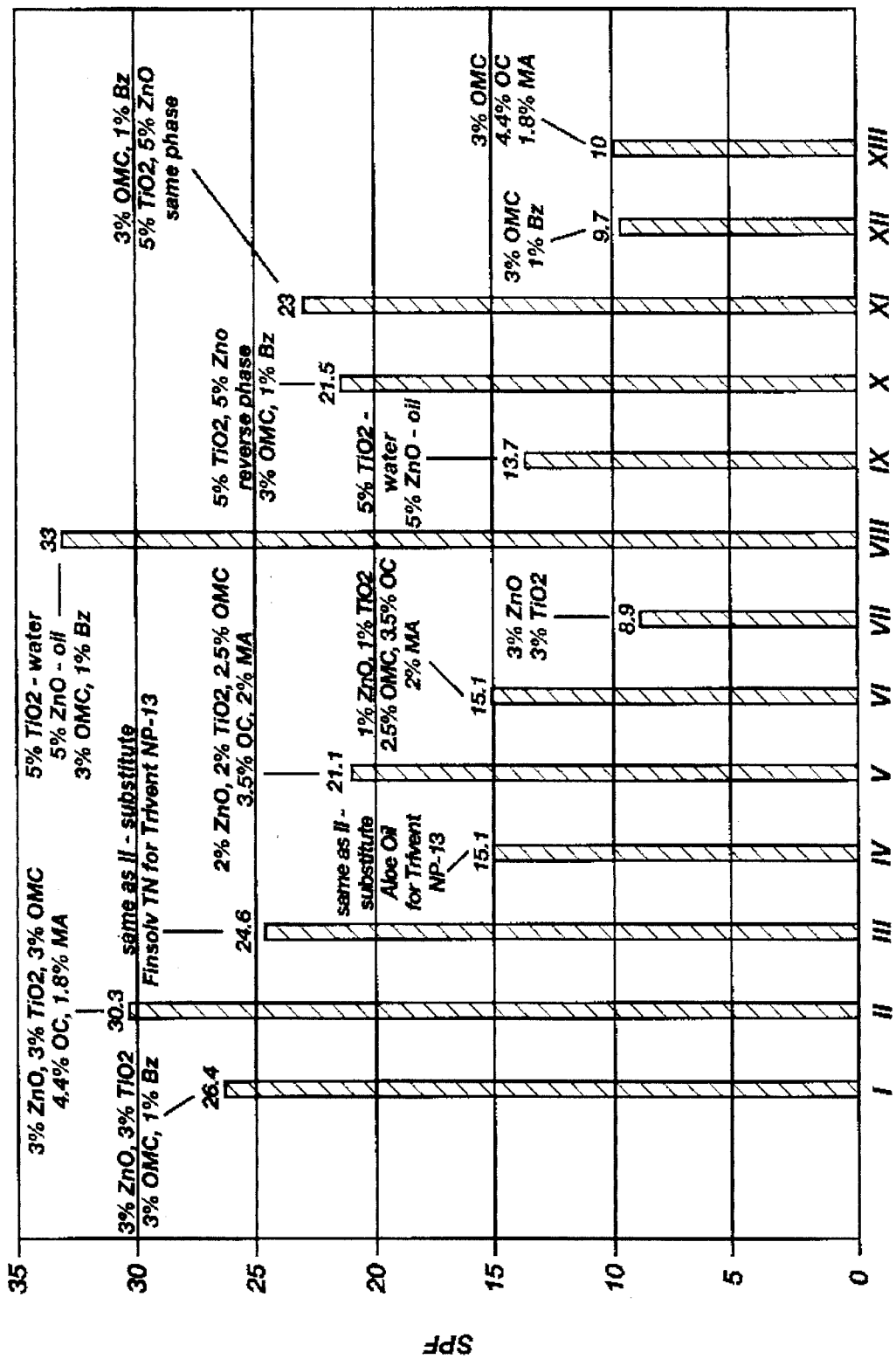
FIG. 1 is a graph depicting the SPF values of various emulsions comprising various organic agents, alone or in combination with $TiO_2$ and ZnO.

The emulsion includes sufficient amounts of the selected ingredients in the appropriate phases to attain a composition having a desired SPF value. In this regard, the emulsion can contain ZnO in an amount up to about 25% and $TiO_2$ in an amount up to about 25%, by weight, of the total emulsion and tridecyl neopentanoate in combination with one or more organic agents. Preferably greater than, 90% of the ZnO will reside in the continuous phase, and 90% of the $TiO_2$ will reside in the discontinuous phase. Percent, as used throughout this specification, refers to weight percent, based on the total weight of the emulsion. The emulsion will preferably contain sufficient amounts of sunblocking agents and oil phase emulsion components to form an oil phase that will produce an emulsion having a smooth, continuous appearance when combined with a water phase.

Preferred organic sunblocking agents include benzophenone-3 (oxybenzone), menthyl anthranilate, octocrylene, octyl methoxycinnamate, and mixtures thereof. Other sunblocking agents such as octyl salicylate, PABA and derivatives may be used. When the emulsion contains octyl methoxycinnamate ("OMC"), an amount up to 7.5%, by weight of the total emulsion may be used. When the emulsion includes benzophenone-3, the emulsion may contain benzophenone-3 in an amount from up to about 6% by weight of the total emulsion.

Preferred oil phase emulsion components include cetyl dimethicone copolyol, cyclomethicone, cetyl dimethicone, hydrogenated castor oil, aloe oil, microcrystalline wax and mixtures thereof.

A preferred method for producing the emulsion involves heating a dispersion medium to the point of melting and then admixing zinc oxide with the dispersion medium. Titanium dioxide is incorporated into a water phase solution. The water phase solution may also include hyaluronic acid and sodium chloride and other water soluble ingredient (e.g. sodium PCA and polyphenon-G). The dispersion medium is then cooled to the approximate temperature of the water phase and both phases are mixed. Alternatively, the water phase may be heated to the approximate temperature of the dispersion medium. To the combined water phase and dispersion medium are then added aluminum starch octenylsuccinate, and preservatives such as propylene glycol, diazolidinyl urea, methylparaben, and propylparaben (Germaben II). A fragrance can also be added, if desired. The resulting emulsion is homogenized for about two minutes.

The dispersion medium may contain tridecyl neopentanoate (or $C_{12-15}$ alkyl benzoate, octyl neopentanoate, or mixtures thereof), benzophenone-3, menthyl anthranilate, octocrylene, octyl methoxycinnamate, cetyl dimethicone copolyol, cyclomethicone, cetyl dimethicone, hydrogenated castor oil, aloe oil, and microcrystalline wax.

The amount of compound such as tridecyl neopentanoate will be sufficient to boost the SPF value, which will typically vary from 0.5 to 20% by weight of the total emulsion, preferably 4 to 10% by weight.

Preferably, the method will use micronized ZnO in an amount from about 1 to about 5% and micronized and coated (e.g. with glycerol, trimethylolethane or dimethicone) $TiO_2$ in an amount from about 1 to 5%, by weight, of the total emulsion. The dispersion medium can usually be melted by heating it to a temperature of about 80° C. The titanium dioxide, hyaluronic acid, and sodium chloride can be readily incorporated into aqueous solution. The water is slowly added to the dispersion medium with rapid stirring. Preferably, the water phase and dispersion medium should be mixed when both are below about 40° C.

$TiO_2$ and ZnO are commercially available under the trade designations "UV-Titan 212", from Presperse Inc., South Plainfield, N.J., and "Z-Cote", from Sun Smart, Inc. of Wainscott, N.Y., respectively.

The following illustrative EXAMPLES represent preferred embodiments of the invention.

EXAMPLE I

A sunscreen formulation in the form of a water-in-oil emulsion was prepared as follows.

| Ingredients | Grams |
|---|---|
| Phase A | |
| Cetyl dimethicone copolyol (Abil Em-90 - Goldschmidt) | 15 |
| Tridecyl neopentanoate (Trivent NP-13 - Trivent) | 20 |
| Cetyl dimethicone (Abil Wax 9801 - Goldschmidt) | 8 |
| Hydrogenated castor oil (castor wax MP 80 - Cas Chem) | 1.5 |
| Microcrystalline wax (victory white wax - Petrolite) | 2 |
| Octyl methoxycinnamate (Escalol 557 - ISP Van Dyk) | 15 |
| Benzophenone-3 (Escalol 567 - ISP Van Dyk) | 5 |
| Tocopheryl acetate (Roche) | 7.5 |
| Aloe vera oil (Aloe Corp.) | 20 |
| Phase B | |
| Zinc oxide (3%) (Z-cote Sun Smart) | 15 |
| Cyclomethicone (Abil B 8839 - Goldschmidt) | 32 |
| Phase C | |
| Deionized water | 322.5 |
| Sodium chloride (Spectrum) | 2.5 |
| Hyaluronic acid (Roche) | 2.5 |
| Polyphenon G (Mitsui Norin) | 0.5 |
| Titanium dioxide (3%) (Titan-212 - Presperse) | 15 |
| Phase D | |
| Aluminum starch octenylsuccinate (Dry Flo PC-National Starch) | 10 |
| Phase E | |
| Fragrance (CE 16356) | 1 |
| Pre blend of | |
| Propylene glycol (Sutton)    (Germaben (II) | 5 |
| diazolidinyl urea (Sutton) | |
| methylparaben (Sutton) | |
| propylparaben (Sutton) | |
| TOTAL WEIGHT | 500 |

Phase A was prepared by melting the listed ingredients together at a temperature of 80° C. Once Phase A melted and mixed, Phase B was added to Phase A with constant stirring. Phase C was then prepared by simple mixing of the ingredients to the deionized water. Once the combined Phase A-B was cooled to below 40° C., Phase C was mixed into the combined Phase A-B. Phase D and Phase E were incorporated into Phase A-B-C by rapid stirring. The resulting mixture was homogenized for two minutes on a Ross mixer.

The SPF value of the formulation (26.4) was determined via an Optometrics SPF-290 Analyzer (available from Optometrics USA, Inc., Ayer, Mass., 01432).

The resulting water-in-oil emulsion is a light tan, viscous liquid, which readily rubbed onto the skin and demonstrated no whitening effect after application. The emulsion was stable.

EXAMPLE II

A sunscreen formulation in the form of a water-in-oil emulsion, having an SPF value of 30.3 was prepared using the methods as described in EXAMPLE I. The ingredients are listed by weight basis in grams. The SPF value was determined in the same manner as in EXAMPLE I.

| Ingredients | Grams |
|---|---|
| Phase A | |
| Cetyl dimethicone copolyol | 15 |
| Tridecyl neopentanoate | 20 |
| Cetyl dimethicone | 8 |
| Cyclomethicone | 32 |
| Hydrogenated castor oil | 1.5 |
| Microcrystalline wax | 2 |
| Octyl methoxycinnamate | 17.5 |
| Tocopheryl acetate | 5 |
| Aloe vera oil | 10 |
| Octocrylene | 22 |
| Menthyl anthranilate | 9 |
| Phase B | |
| Zinc oxide (3%) | 15 |
| Phase C | |
| Deionized water | 308 |
| Sodium chloride | 2.5 |
| Hyaluronic acid | 2.5 |
| Titanium dioxide (3%) | 15 |
| Phase D | |
| Aluminum starch octenylsuccinate | 10 |
| Phase E | |
| Pre blend of | |
| Propylene glycol (Germaben II) | 5 |
| diazolidinyl urea | |
| methylparaben | |
| propylparaben | |
| TOTAL WEIGHT | 500 |

The emulsion of EXAMPLE II was a white viscous liquid similar to EXAMPLE I, except for the added benefit of a higher SPF value.

EXAMPLE III

A sunscreen formulation in the form of a water-in-oil emulsion, having an SPF value of 24.6 was prepared using the methods similar to those of EXAMPLE I. The SPF value was determined in the same manner as in EXAMPLE I.

| Ingredients | Grams |
|---|---|
| Phase A | |
| Cetyl dimethicone copolyol | 15 |
| C$_{12-15}$ alkyl benzoate (Finsolu TN - Finetex Elmwood Park, NJ) | 20 |
| Cetyl dimethicone | 8 |
| Cyclomethicone | 32 |
| Hydrogenated castor oil | 1.5 |
| Microcrystalline wax | 2 |
| Octyl methoxycinnamate | 17.5 |
| Tocopheryl acetate | 5 |
| Aloe vera oil | 10 |
| Octocrylene | 22 |
| Menthyl anthranilate | 9 |
| Phase B | |
| Zinc oxide (3%) | 15 |
| Phase C | |
| Deionized water | 301.5 |
| Sodium chloride | 2.5 |
| Hyaluronic acid | 2.5 |
| Titanium dioxide (3%) | 15 |
| Phase D | |
| Aluminum starch octenylsuccinate | 10 |
| Phase E | |
| Pre blend of | |
| Propylene glycol (Germaben II) | 5 |
| diazolidinyl urea | |
| methylparaben | |
| propylparaben | |
| TOTAL WEIGHT | 500 |

The method of EXAMPLE III resulted in a lustrous, white, soft cream. Upon an additional two minute period of homogenization on a Ross mixer, the cream became thinner, readily rubbed onto the skin, and had a creamy but non-greasy feel. The cream does not create a white film when applied to the skin. The SPF value of the cream in this example was lower than the SPF value of EXAMPLE I.

EXAMPLE IV

A sunscreen formulation in the form of a water-in-oil emulsion, having an SPF value of 15.1 was prepared using the methods as described in EXAMPLE I. The SPF value was determined in the same manner as in EXAMPLE I.

| Ingredients | Grams |
|---|---|
| Phase A | |
| Cetyl dimethicone copolyol | 15 |
| Cetyl dimethicone | 8 |
| Cyclomethicone | 32 |
| Hydrogenated castor oil | 1.5 |
| Microcrystalline wax | 2 |
| Octyl methoxycinnamate | 17.5 |
| Tocopheryl acetate | 5 |
| Aloe vera oil | 30 |
| Octocrylene | 22 |
| Menthyl anthranilate | 9 |
| Phase B | |
| Zinc oxide (3%) | 15 |
| Phase C | |
| Deionized water | 308 |
| Sodium chloride | 2.5 |
| Hyaluronic acid | 2.5 |
| Titanium dioxide (3%) | 15 |
| Phase D | |
| Aluminum starch octenylsuccinate | 10 |
| Phase E | |
| Pre blend of | |
| Propylene glycol (Germaben II) | 5 |
| diazolidinyl urea | |
| methylparaben | |
| propylparaben | |
| TOTAL WEIGHT | 500 |

The emulsion of EXAMPLE IV was substantially indistinguishable from the emulsion described in EXAMPLE III except for having a lower SPF value.

EXAMPLE V

A sunscreen formulation in the form of a water-in-oil emulsion, having an SPF value of 21.1 was prepared using the methods similar to those of EXAMPLE I. The SPF value was determined in the same manner as in EXAMPLE I.

| Ingredients | Grams |
|---|---|
| Phase A | |
| Cetyl dimethicone copolyol | 15 |
| Tridecyl neopentanoate | 20 |
| Cetyl dimethicone | 8 |
| Cyclomethicone | 32 |
| Hydrogenated castor oil | 1.5 |
| Microcrystalline wax | 2 |
| Octyl methoxycinnamate | 12.5 |
| Tocopheryl acetate | 5 |
| Aloe vera oil | 10 |
| Octocrylene | 17.5 |
| Menthyl anthranilate | 10 |
| Phase B | |
| Zinc oxide (2%) | 10 |
| Phase C | |
| Deionized water | 325.5 |
| Sodium chloride | 2.5 |
| Hyaluronic acid | 2.5 |
| Titanium dioxide (2%) | 10 |
| Phase D | |
| Aluminum starch octenylsuccinate | 10 |
| Phase E | |
| Fragrance (CE 16356) | 1 |
| Pre blend of | |
| Propylene glycol (Germaben II) | 5 |
| diazolidinyl urea | |
| methylparaben | |
| propylparaben | |
| TOTAL WEIGHT | 500 |

The emulsion of EXAMPLE V was substantially indistinguishable from the emulsion described in EXAMPLE 3 except for having a lower SPF value.

EXAMPLE VI

A sunscreen formulation in the form of a water-in-oil emulsion, having an SPF value of 15.1 was prepared in a manner similar to EXAMPLE I. The SPF value was determined in the same manner as in EXAMPLE I.

| Ingredients | Grams |
|---|---|
| Phase A | |
| Cetyl dimethicone copolyol | 15 |
| Tridecyl neopentanoate | 20 |
| Cetyl dimethicone | 8 |
| Cyclomethicone | 32 |
| Hydrogenated castor oil | 1.5 |
| Microcrystalline wax | 2 |
| Octyl methoxycinnamate | 12.5 |
| Tocopheryl acetate | 5 |
| Aloe vera oil | 10 |
| Octocrylene | 17.5 |
| Menthyl anthranilate | 10 |
| Phase B | |
| Zinc oxide (1%) | 5 |
| Phase C | |
| Deionized water | 336.5 |
| Sodium chloride | 2.5 |
| Hyaluronic acid | 2.5 |
| Titanium dioxide (1%) | 5 |
| Phase D | |
| Aluminum starch octenylsuccinate | 10 |
| Phase E | |
| Pre blend of | |
| Propylene glycol (Germaben II) | 5 |
| diazolidinyl urea | |
| methylparaben | |
| propylparaben | |
| TOTAL WEIGHT | 500 |

The emulsion of EXAMPLE VI was substantially indistinguishable from the emulsion described in EXAMPLE III, except for having a lower SPF value.

EXAMPLE VII

A sunscreen formulation in the form of a water-in-oil emulsion, having an SPF value of 8.9 was prepared using the identical methods as described in EXAMPLE I. The ingredients are listed by weight basis in grams. The SPF value was determined in the same manner as in EXAMPLE I.

| Ingredients | Grams |
|---|---|
| Phase A | |
| Cetyl dimethicone copolyol | 20 |
| Tridecyl neopentanoate | 25 |
| Cetyl dimethicone | 8 |
| Cyclomethicone | 32 |
| Hydrogenated castor oil | 1.5 |
| Microcrystalline wax | 2 |
| Tocopheryl acetate | 7.5 |
| Aloe vera oil | 25 |
| Phase B | |
| Zinc oxide (3%) | 15 |
| Phase C | |
| Deionized water | 329 |
| Sodium chloride | 2.5 |
| Hyaluronic acid | 2.5 |
| Titanium dioxide (3%) | 15 |
| Phase D | |
| Aluminum starch octenylsuccinate | 10 |
| Phase E | |
| Pre blend of | |
| Propylene glycol (Germaben II) | 5 |
| diazolidinyl urea | |
| methylparaben | |
| propylparaben | |
| TOTAL WEIGHT | 500 |

The emulsion of EXAMPLE VII was substantially indistinguishable from the emulsion described in EXAMPLE 3, except for having a much lower SPF value.

EXAMPLE VIII

A sunscreen formulation in the form of a water-in-oil emulsion, having an SPF value of 33 was prepared using the methods similar to those of EXAMPLE I. The ingredients are listed by weight basis in grams. The SPF value was determined in the same manner as in EXAMPLE I.

| Ingredients | Grams |
| --- | --- |
| Phase A | |
| Cetyl dimethicone copolyol | 20 |
| Tridecyl neopentanoate | 25 |
| Cetyl dimethicone | 12 |
| Cyclomethicone | 32 |
| Hydrogenated castor oil | 2 |
| Microcrystalline wax | 4 |
| Aloe vera oil | 25 |
| Octyl methoxycinnamate | 15 |
| Benzophenone-3 | 5 |
| Phase B | |
| Zinc oxide (5%) | 25 |
| Phase C | |
| Deionized water | 291 |
| Sodium chloride | 3 |
| Titanium dioxide (5%) | 25 |
| Phase D | |
| Aluminum starch octenylsuccinate | 10 |
| Phase E | |
| Fragrance (CE 16356) | 1 |
| Pre blend of | |
| Propylene glycol  (Germaben II) | 5 |
| diazolidinyl urea | |
| methylparaben | |
| propylparaben | |
| TOTAL WEIGHT | 500 |

The emulsion of EXAMPLE VIII was substantially indistinguishable from the emulsion described in EXAMPLE III, except for having a higher SPF value.

EXAMPLE IX

A sunscreen formulation in the form of a water-in-oil emulsion, having an SPF value of 13.7 was prepared using methods similar to those of EXAMPLE I. The SPF value was determined in the same manner as in EXAMPLE I.

| Ingredients | Grams |
| --- | --- |
| Phase A | |
| Cetyl dimethicone copolyol | 16 |
| Tridecyl neopentanoate | 24.8 |
| Cetyl dimethicone | 9.6 |
| Cyclomethicone | 25.6 |
| Hydrogenated castor oil | 1.6 |
| Microcrystalline wax | 3.2 |
| Aloe vera oil | 20 |
| Phase B | |
| Zinc oxide (5%) | 20 |
| Phase C | |
| Deionized water | 236.8 |
| Sodium chloride | 1.6 |
| Titanium dioxide (5%) | 20 |
| Phase D | |
| Aluminum starch octenylsuccinate | 16 |
| Phase E | |
| Fragrance (CE 16356) | 0.8 |
| Pre blend of | |
| Propylene glycol  (Germaben II) | 4 |
| diazolidinyl urea | |
| methylparaben | |
| propylparaben | |
| TOTAL WEIGHT | 400 |

The emulsion of EXAMPLE IX was substantially indistinguishable from the emulsion described in EXAMPLE III, except for having a lower SPF value.

EXAMPLE X

In this EXAMPLE, the same methods and ingredients were used as described in EXAMPLE VIII except that the ZnO and $TiO_2$ were introduced into the reverse phases. 25 grams of $TiO_2$ replaced the ZnO in Phase B and 25 grams of ZnO replaced the $TiO_2$ in Phase C. The emulsion of EXAMPLE X was substantially indistinguishable from the emulsion of EXAMPLE VIII except for a decrease in SPF from 33, seen in the emulsion of EXAMPLE VIII, to 21.5.

EXAMPLE XI

In this EXAMPLE, the same methods and ingredients were used as described in EXAMPLE VIII except that the ZnO and $TiO_2$ were both introduced into the same phase. Phase B consisted of 25 grams of $TiO_2$ and ZnO, respectively. The emulsion of EXAMPLE XI was substantially indistinguishable from the emulsion described in EXAMPLE VIII except for a decrease in SPF from 33, seen in the emulsion of EXAMPLE VIII, to 23.

EXAMPLE XII

A sunscreen formulation in the form of a water-in-oil emulsion, having an SPF value of 9.7 was prepared using the methods similar to those of EXAMPLE I. The SPF value was determined in the same manner as in EXAMPLE I.

| Ingredients | Grams |
| --- | --- |
| Phase A | |
| Cetyl dimethicone copolyol (Abil Em-90 - Goldschmidt) | 20 |
| Tridecyl neopentanoate (Ceruphyl 55) | 25 |
| Cetyl dimethicone (Abil Wax 9801 - Goldschmidt) | 12 |
| Hydrogenated castor oil (castor wax MP 80 - Cas Chem) | 2 |
| Microcrystalline wax (victory white wax - Petrolite) | 4 |
| Octyl methoxycinnamate (Escalol 557 - ISP Van Dyk) | 15 |
| Benzophenone-3 (Escalol 567 - ISP Van Dyk) | 5 |
| Aloe vera oil (Aloe Corp.) | 25 |
| Cyclomethicone (Abil B 8839 - Goldschmidt) | 32 |
| Phase B | |
| Deionized water | 341 |
| Sodium chloride (Spectrum) | 3 |
| Phase C | |
| Aluminum starch octenylsuccinate (Dry Flo PC-National Starch) | 10 |
| Phase D | |
| Pre blend of | |
| Propylene glycol (Sutton)  (Germaben (II)) | 5 |
| diazolidinyl urea (Sutton) | |
| methylparaben (Sutton) | |
| propylparaben (Sutton) | |
| | 499 |

EXAMPLE XIII

A sunscreen formulation in the form of a water-in-oil emulsion, having an SPF value of 10 was prepared using methods similar to those as described in EXAMPLE I. The ingredients are listed by weight basis in grams. The SPF value was determined in the same manner as in EXAMPLE I.

| Ingredients | Grams |
| --- | --- |
| Phase A | |
| Cetyl dimethicone copolyol | 15 |
| Tridecyl neopentanoate | 20 |
| Cetyl dimethicone | 8 |
| Cyclomethicone | 32.6 |
| Hydrogenated castor oil | 1.5 |
| Microcrystalline wax | 2 |
| Octyl methoxycinnamate | 17.5 |
| Tocopheryl acetate | 5 |
| Aloe vera oil | 10 |
| Octocrylene | 22 |
| Menthyl anthranilate | 9 |
| Phase B | |
| Deionized water | 331.5 |
| Sodium chloride | 2.5 |
| Hyaluronic acid | 2.5 |
| Phase C | |
| Aluminum starch octenylsuccinate | 10 |
| Phase D | |
| Pre blend of | |
| Propylene glycol   (Germaben II) | 5 |
| diazolidinyl urea | |
| methylparaben | |
| propylparaben | |
| | 494 |

Phase A was heated to melt the solid ingredients and then stirred to cool. Phase B was added slowly with rapid stirring followed by C and then D. The product is a lustrous, off-white, soft cream with an easy rob-in and soft dry after feel.

EXAMPLE XIV

A five panel skin test of the emulsion of EXAMPLE VIII was conducted according to the "Proposed Monograph for UTC Sunscreen Products" issued by the Food & Drug Administration, Aug. 25, 1978, *Federal Register*, 43 (166): 38206–38269. An SPF value of 30.2 was measured.

EXAMPLE XV

An oil-in-water emulsion containing 3% ZnO in the oil phase, 3% $TiO_2$ in the water phase, and 3% octylmethoxycinnamate and 1% benzophenone-3 was made. It had an SPF value of 17.7.

| Ingredients | Grams |
| --- | --- |
| Phase A | |
| Stearic Acid | 21 |
| Octyl Methoxycinnamate | 15 |
| Arlacel 165 | 22 |
| Ceraphyl 55 | 20 |
| Benzophenone-3 | 5 |
| Cetyl Alcohol | 5 |
| Dow Corning 225 | 5 |
| Tween 60 | 2.5 |
| Phase B | |
| Z-Cote (ZnO) | 15 |
| Phase C | |
| Deionized water | 334.6 |
| Aloe Powder | .15 |
| Glycerin | 2.5 |
| Germaben II | 5 |
| Carbomer 980 (3% Soln) | 5 |
| Veegum Ultra (4% Susp) | 3.75 |
| UV Titan M212 ($TiO_2$) | 15 |
| Phase D | |
| Triethanolamine | 3.5 |
| Deionized Water | 10 |
| Phase E | |
| DryFlo | 10 not added |

Phase A was heated to melt the ingredients (80° C.) and B added with stirring. Phase C was stirred magnetically and heated to 75° C. While being constantly stirred, it was added to the A-B mixture. Phase D was added and stirred to cool (~40° C.). No Dry Flo was added. The thin white liquid was hand homogenized twice and 1% sepigel 305 added to thicken.

EXAMPLE XVI

An oil-in-water emulsion containing 3% ZnO in the water phase, 3% $TiO_2$ in the oil phase, and 3% octyl methoxycinnamate and 1% benzophenone was made. It had an SPF value of 19.2.

| Ingredients | Grams |
| --- | --- |
| Phase A | |
| Stearic Acid | 21 |
| Octyl Methoxycinnamate | 15 |
| Arlacel 165 | 22 |
| Ceraphyl 55 | 20 |
| Benzophenone-3 | 5 |
| Cetyl Alcohol | 5 |
| Dow Corning 225 | 5 |
| Tween 60 | 2.5 |
| Phase B | |
| UV Titan M212 ($TiO_2$) | 15 |
| Phase C | |
| Deionized water | 334.6 |
| Aloe Powder | .15 |
| Glycerin | 2.5 |
| Germaben II | 5 |
| Carbomer 980 (3% Soln) | 5 |
| Veegum Ultra (4% Susp) | 3.75 |
| Z-Cote (ZnO) | 15 |
| Phase D | |
| Triethanolamine | 3.5 |
| Deionized Water | 10 |
| Phase E | |
| Dry Flo | 10 not added |

Phase A was heated to melt the ingredients (80° C.) and B added with stirring. Phase C was stirred magnetically and heated to 75° C. While being constantly stirred, it was added to the A-B mixture. Phase D was added and stirred to cool (−40° C.). No Dry Flo was added. The thin white liquid was hand homogenized twice and 1% Sepigel 305 added to thicken. References herein to specific EXAMPLES or embodiments should not be interpreted as limitations to the invention's scope, which is to be determined by the claims.

What is claimed is:

1. A water-in-oil emulsion comprising zinc oxide, present in an amount from about 0.1 to about 25% by weight of the water-in-oil emulsion, and an agent selected from the group consisting of tridecyl neopentanoate, $C_{12-15}$ alkyl benzoate, octyl neopentanoate and mixtures thereof in the emulsion's oil phase, titanium dioxide in the emulsion's water phase, said titanium dioxide present in an amount from about 0.1 to about 25% by weight of the water-in-oil emulsion, a sunblocking agent, and oil phase emulsion components.

2. The water-in-oil emulsion of claim 1, wherein said oil phase emulsion components are selected from the group consisting of cetyl dimethicone copolyol, cyclomethicone, cetyl dimethicone, hydrogenated castor oil, aloe oil, microcrystalline wax and mixtures thereof.

3. The water-in-oil emulsion of claim 1, wherein said sunblocking agent is selected from the group consisting of oxybenzone, menthyl anthranilate, octocrylene, octyl methoxycinnamate, and mixtures thereof.

4. The water-in-oil emulsion of claim 1, wherein said water-in-oil emulsion produces a sun protection factor value of 30 or more, as determined by an instrumental sun protection factor analyzer, and filters light radiation in the range of from about 280 to about 320 nm.

5. The water-in-oil emulsion of claim 3, wherein the water-in-oil emulsion contains octyl methoxycinnamate present in an amount from about 0.1 to about 7.5% by weight.

6. The water-in-oil emulsion of claim 3, wherein the water-in-oil emulsion contains oxybenzone present in an amount from about 0.1 to about 6% by weight.

7. A method for producing a water-in-oil emulsion of claim 1 comprising:

heating a dispersion medium comprising members selected from the group consisting of tridecyl neopentanoate, $C_{12-15}$ alkyl benzoate, octyl neopentanoate, oxybenzone, menthyl anthranilate, octocrylene, octyl methoxycinnamate, cetyl dimethicone copolyol, cyclomethicone, cetyl dimethicone, hydrogenated castor oil, aloe oil, microcrystalline wax, and mixtures thereof until said dispersion medium melts; admixing into the melted dispersion medium up to 25% of ZnO by weight; making a water phase comprising water, $TiO_2$, hyaluronic acid, and sodium chloride; cooling said dispersion medium; mixing said water phase with said dispersion medium admixture; admixing aluminum starch octenylsuccinate, propylene glycol, diazolidinyl urea, methylparaben, and propylparaben with said dispersion medium; and homogenizing said medium to form said water-in-oil emulsion.

8. The method according to claim 7, wherein said dispersion medium is heated to about 80° C. in order to melt said dispersion medium.

9. The method according to claim 7, wherein said dispersion medium is cooled to less than 40° C. and said water phase is added.

10. The method according to claim 7, wherein said octyl methoxycinnamate is present in an amount from about 0.1 to about 7.5%, by weight of the total emulsion.

11. The method according to claim 7, wherein said oxybenzone is present in an amount from about 0.1 to 6%, by weight of the total emulsion.

12. The method according to claim 11, wherein said emulsion has a sun protection factor value of 30 or above, as measured by an instrumental sun protector factor analyzer, and filters light radiation in the range of from about 280 to about 320 nm.

13. A method of increasing the sun protection factor value of an emulsion having a continuous phase and a discontinuous phase, said method comprising: incorporating $TiO_2$ in an amount from 0.1 to 25% by weight of the emulsion into the emulsion's discontinuous phase; and incorporating ZnO in an amount from 0.1 to 25% by weight of the emulsion into the emulsion's continuous phase.

14. The method of claim 13, wherein said emulsion's discontinuous phase is aqueous.

15. The method of claim 13, wherein the discontinuous phase is an oil phase.

16. A method of using the water-in-oil emulsion of claim 1, comprising applying said water-in-oil emulsion to mammalian skin.

17. An improvement in a sunscreen emulsion having a continuous phase and a discontinuous phase, the improvement comprising having from about 0.1 to about 25% by weight of the sunscreen emulsion $TiO_2$ in the discontinuous phase and having from about 0.1 to about 25% by weight of the sunscreen emulsion ZnO in the continuous phase.

\* \* \* \* \*

UNITED STATES PATENT AND TRADEMARK OFFICE
CERTIFICATE OF CORRECTION

PATENT NO. : 5,543,136
DATED : August 6, 1996
INVENTOR(S) : Duane L. Aldous

It is certified that error appears in the above-indentified patent and that said Letters Patent is hereby corrected as shown below:

col. 1, line 14, change "bums" to --burns--;

col. 1, line 46, change "robbed" to --rubbed--;

col. 3, line 8, delete the comma after "than";

col. 10, line 9, change "1II" to --III--; and col. 11, line 40, change "rob-in" to --rub-in--.

Signed and Sealed this

Twenty-sixth Day of November 1996

Attest:

BRUCE LEHMAN

Attesting Officer

Commissioner of Patents and Trademarks